(12) United States Patent
Liu et al.

(10) Patent No.: US 12,735,384 B2
(45) Date of Patent: Sep. 15, 2026

(54) METHODS FOR PREPARING (2S,3R,4R)-4,5-DIHYDROXYISOLEUCINE DERIVATIVE AND INTERMEDIATES THEREOF

(71) Applicants: INNER MONGOLIA UNIVERSITY, Huhhot (CN); INNER MONGOLIA DUHE INNOVATION R & D TECH CO., LTD, Huhhot (CN)

(72) Inventors: Guodu Liu, Huhhot (CN); Zongwei Li, Huhhot (CN); Xinlong Yan, Huhhot (CN)

(73) Assignees: INNER MONGOLIA UNIVERSITY, Huhhot (CN); INNER MONGOLIA DUHE INNOVATION R & D TECH CO., LTD, Huhhot (CN)

( * ) Notice: Subject to any disclaimer, the term of this patent is extended or adjusted under 35 U.S.C. 154(b) by 58 days.

(21) Appl. No.: 18/994,172

(22) PCT Filed: Jun. 4, 2024

(86) PCT No.: PCT/CN2024/097162

§ 371 (c)(1),
(2) Date: Jan. 14, 2025

(87) PCT Pub. No.: WO2024/188374

PCT Pub. Date: Sep. 19, 2024

(65) Prior Publication Data

US 2026/0001836 A1 Jan. 1, 2026

(30) Foreign Application Priority Data

Mar. 7, 2024 (CN) ......................... 202410257052.0

(51) Int. Cl.

| | |
|---|---|
| ***C07C 269/06*** | (2006.01) |
| ***B01J 31/18*** | (2006.01) |
| ***B01J 31/22*** | (2006.01) |
| ***C07C 249/02*** | (2006.01) |
| ***C07C 251/24*** | (2006.01) |

(52) U.S. Cl.

CPC ......... *C07C 269/06* (2013.01); *B01J 31/1805* (2013.01); *B01J 31/2295* (2013.01); *C07C 249/02* (2013.01); *C07C 251/24* (2013.01); *B01J 2231/44* (2013.01); *B01J 2531/004* (2013.01); *B01J 2531/16* (2013.01); *B01J 2531/822* (2013.01); *C07C 2603/18* (2017.05)

(58) Field of Classification Search

CPC ... C07C 269/06; C07C 249/02; C07C 251/24; C07C 2603/18; C07C 227/32; C07C 229/36; C07C 271/22; C07C 269/04; B01J 31/1805; B01J 31/2295; B01J 2231/44; B01J 2531/004; B01J 2531/16; B01J 2531/822; B01J 31/2282; Y02P 20/55

See application file for complete search history.

(56) References Cited

FOREIGN PATENT DOCUMENTS

| | | | |
|---|---|---|---|
| CN | 112525116 | A | 3/2021 |
| CN | 112585116 | A | 3/2021 |
| CN | 114080395 | A | 2/2022 |
| CN | 117843525 | A | 4/2024 |
| EP | 3 747 886 | A1 | 12/2020 |

OTHER PUBLICATIONS

Siegert et al: "A Convergent Total Synthesis of the Death Cap Toxin a-Amanitin", Angew. Chem. Int. Ed., vol. 59, No. 132, p. 5500-5504. (Year: 2020).*

Siegert et al: "A Convergent Total Synthesis of the Death Cap Toxin a-Amanitin", Angew. Chem. Int. Ed., vol. 59, No. 132, p. 5500-5504, Feb. 6, 2020.

Wang et al: "Synthessi of [beta]-anti-Substituted [alpha]-Amino Acides through Iridium-Catalyzed Alkylation/ Chelation-Controlled Nucleophilic Addition", SYNLETT, vol. 33, p. 655-658, 2022.

Xia et al: "Mechanistic Study of Ni and Cu Dual Catalyst for Asymmetric C—C Bond Formation; Asymmetric Coupling of 1,3-Dienes with C-nucleophiles to Construct Vicinal Stereocenters", ACS Catalysis, vol. 11, p .6643-6655, May 21, 2021.

* cited by examiner

*Primary Examiner* — Deborah D Carr
(74) *Attorney, Agent, or Firm* — WCF IP

(57) ABSTRACT

Provided are methods for preparing a (2S,3R,4R)-4,5-dihydroxyisoleucine (DHile) derivative and intermediates thereof. Methods for preparing a series of intermediates of the (2S,3R,4R)-4,5-DHile derivative are provided, on the basis of which the (2S,3R,4R)-4,5-DHile derivative could be prepared. Specifically, a glycine derivative, benzophenone imine glycine tert-butyl ester (compound 1, with a structure shown in Formula 1) that is easy to be purchased through commercial channels and has a low price, is selected as a starting reaction raw material; the starting reaction raw material is subjected to asymmetric allylation, asymmetric dihydroxylation, and introduction or removal of protective groups to achieve efficient asymmetric synthesis of a target product.

Formula 1

4 Claims, No Drawings

METHODS FOR PREPARING (2S,3R,4R)-4,5-DIHYDROXYISOLEUCINE DERIVATIVE AND INTERMEDIATES THEREOF

CROSS-REFERENCE TO RELATED APPLICATION

The present application is a national stage application of International Patent Application No. PCT/CN2024/097162, filed on Jun. 4, 2024, which claims priority to Chinese Patent Application No. CN202410257052.0 filed to the China National Intellectual Property Administration (CNIPA) on Mar. 7, 2024 and entitled "METHODS FOR PREPARING (2S,3R,4R)-4,5-DIHYDROXYISOLEUCINE DERIVATIVE AND INTERMEDIATES THEREOF". The two applications each are incorporated herein by reference in its entirety.

TECHNICAL FIELD

The present disclosure relates to the technical field of organic synthesis, and in particular to methods for preparing a (2S,3R,4R)-4,5-dihydroxyisoleucine derivative and intermediates thereof.

BACKGROUND

Amino acids are not only important components of macromolecules in organisms, but also have wide applications in the field of organic synthesis and medicine. However, there are only a few naturally occurring amino acids. Modifications of the natural amino acids could produce a range of unnatural amino acids. Most amino acids are chiral amino acids, and it has always been one of the hot spots and difficulties in organic synthesis research to obtain non-natural amino acids with a high optical purity. For example, chiral dihydroxyisoleucine (DHile), an unnatural amino acid with three chiral centers, is not commercially available. The chiral DHile shows important applications in the synthesis of polypeptides such as cyclic peptide toxin compounds. However, no effective method has been found to obtain the DHile with a low production cost and a high optical purity.

SUMMARY

An object of the present disclosure is to provide methods for preparing a (2S,3R,4R)-4,5-dihydroxyisoleucine ((2S,3R,4R)-4,5-DHile) derivative and intermediates thereof. The (2S, 3R, 4R)-4,5-DHile derivative and the intermediates thereof prepared by the methods of the present disclosure have a high optical purity and a low production cost.

To achieve the above object the present disclosure provides the following technical solutions:

Provided is a method for preparing an intermediate A of a (2S,3R,4R)-4,5-DHile derivative, including the following steps:

subjecting a compound 1 to asymmetric allylation to obtain the intermediate A of the (2S,3R,4R)-4,5-DHile derivative; where the compound 1 has a structure shown in Formula 1, and the intermediate A of the (2S,3R,4R)-4,5-DHile derivative has a structure shown in Formula 2:

Formula 1

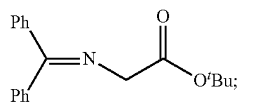

Formula 2

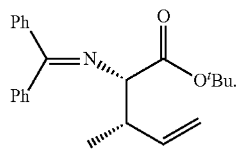

Further provided is a method for preparing an intermediate A' of the (2S,3R,4R)-4,5-DHile derivative, including the following steps:

preparing the intermediate A of the (2S,3R,4R)-4,5-DHile derivative by the method described above; and subjecting the intermediate A of the (2S,3R,4R)-4,5-DHile derivative to imine hydrolysis and 9-fluorenylmethoxycarbonyl (Fmoc) protection to obtain the intermediate A' of the (2S,3R,4R)-4,5-DHile derivative; where the intermediate A' of the (2S,3R,4R)-4,5-DHile derivative has a structure shown in Formula 2':

Formula 2′

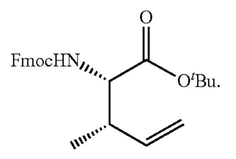

Further provided is a method for preparing an intermediate B of the (2S,3R,4R)-4,5-DHile derivative, including the following steps:

preparing the intermediate A of the (2S,3R,4R)-4,5-DHile derivative by the method described above; and subjecting the intermediate A of the (2S,3R,4R)-4,5-DHile derivative to asymmetric dihydroxylation to obtain the intermediate B of the (2S,3R,4R)-4,5-DHile derivative; where the intermediate B of the (2S,3R,4R)-4,5-DHile derivative has a structure shown in Formula 3:

Formula 3

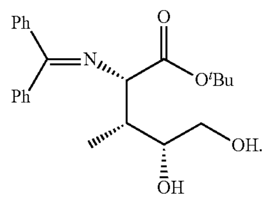

Further provided is a method for preparing an intermediate C of a (2S,3R,4R)-4,5-DHile derivative, including the following steps:

preparing the intermediate B of the (2S,3R,4R)-4,5-DHile derivative by the method described above; and subjecting the intermediate B of the (2S,3R,4R)-4,5-DHile derivative to imine hydrolysis and 9-fluorenylmethoxycarbonyl (Fmoc) protection to obtain the intermediate C of the (2S,3R,4R)-4,5-DHile derivative; where the intermediate C of the (2S,3R,4R)-4,5-DHile derivative has a structure shown in Formula 4:

Formula 4

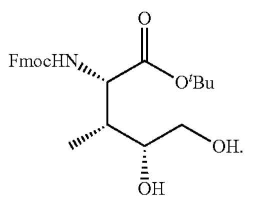

Further provided is a method for preparing an intermediate C of a (2S,3R,4R)-4,5-DHile derivative, including the following steps:

preparing the intermediate A' of the (2S,3R,4R)-4,5-DHile derivative by the method described above; and subjecting the intermediate A' of the (2S,3R,4R)-4,5-DHile derivative to asymmetric dihydroxylation to obtain the intermediate C of the (2S,3R,4R)-4,5-DHile derivative; where the intermediate C of the (2S,3R,4R)-4,5-DHile derivative has a structure shown in Formula 4:

Formula 4

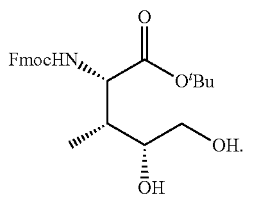

Further provided is a method for preparing a (2S,3R,4R)-4,5-DHile derivative, including the following steps:

preparing the intermediate A of the (2S,3R,4R)-4,5-DHile derivative by a method described above;

subjecting the intermediate A of the (2S,3R,4R)-4,5-DHile derivative to asymmetric dihydroxylation to obtain an intermediate B of the (2S,3R,4R)-4,5-DHile derivative;

subjecting the intermediate B of the (2S,3R,4R)-4,5-DHile derivative to imine hydrolysis and Fmoc protection to obtain an intermediate C of the (2S,3R,4R)-4,5-DHile derivative;

subjecting the intermediate C of the (2S,3R,4R)-4,5-DHile derivative to acetylation to obtain an intermediate D of the (2S,3R,4R)-4,5-DHile derivative; and subjecting the intermediate D of the (2S,3R,4R)-4,5-DHile derivative to tert-butyl ester hydrolysis to obtain the (2S,3R,4R)-4,5-DHile derivative; where the compound 1, the intermediate A of the (2S,3R,4R)-4,5-DHile derivative, the intermediate B of the (2S,3R,4R)-4,5-DHile derivative, the intermediate C of the (2S,3R,4R)-4,5-DHile derivative, the intermediate D of the (2S,3R,4R)-4,5-DHile derivative, and the (2S,3R,4R)-4,5-DHile derivative have structures shown in Formula 1, Formula 2, Formula 3, Formula 4, Formula 5, and Formula 6, respectively:

Formula 1

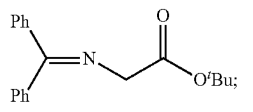

Formula 2

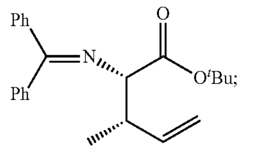

Formula 3

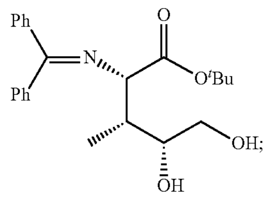

Formula 4

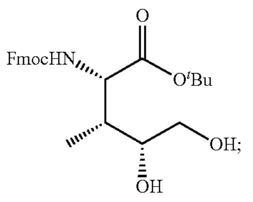

Formula 5

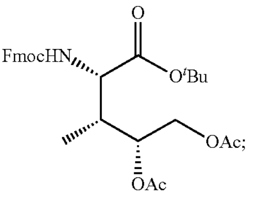

Formula 6

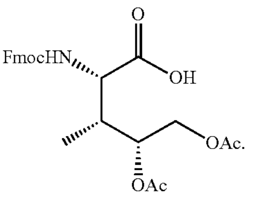

Further provided is a method for preparing a (2S,3R,4R)-4,5-DHile derivative, including the following steps:

preparing the intermediate A of the (2S,3R,4R)-4,5-DHile derivative by a method described above;

subjecting the intermediate A of the (2S,3R,4R)-4,5-DHile derivative to imine hydrolysis and 9-fluorenylmethoxycarbonyl (Fmoc) protection to obtain an intermediate A' of the (2S,3R,4R)-4,5-DHile derivative;

subjecting the intermediate A' of the (2S,3R,4R)-4,5-DHile derivative to asymmetric dihydroxylation to obtain an intermediate C of the (2S,3R,4R)-4,5-DHile derivative;

subjecting the intermediate C of the (2S,3R,4R)-4,5-DHile derivative to acetylation to obtain an intermediate D of the (2S,3R,4R)-4,5-DHile derivative; and subjecting the intermediate D of the (2S,3R,4R)-4,5-DHile derivative to tert-butyl ester hydrolysis to obtain the (2S,3R,4R)-4,5-DHile derivative; where the compound 1, the intermediate A of the (2S,3R,4R)-4,5-DHile derivative, the intermediate A' the (2S,3R,4R)-4,5-DHile derivative, the intermediate C of the (2S,3R,4R)-4,5-DHile derivative, the intermediate D of the (2S,3R,4R)-4,5-DHile derivative, and the (2S,3R,4R)-4,5-DHile derivative have structures shown in Formula 1, Formula 2, Formula 2', Formula 4, Formula 5, and Formula 6, respectively:

Formula 1

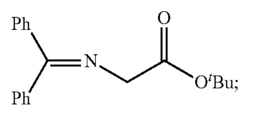

Formula 2

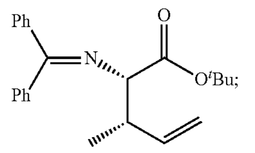

Formula 2'

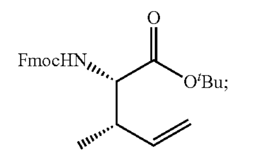

Formula 4

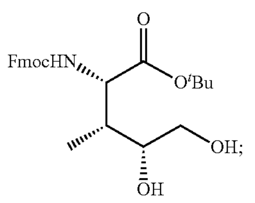

Formula 5

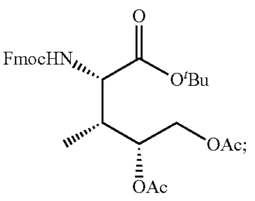

Formula 6

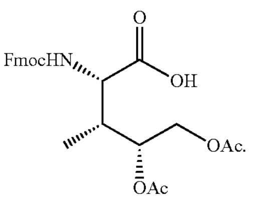

In some embodiments, a raw material for the asymmetric allylation includes 3-chlorobut-1-ene; and the asymmetric allylation is conducted in the presence of a rhodium catalyst, a rhodium catalyst ligand, a copper catalyst, a copper catalyst ligand, and an alkaline reagent.

In some embodiments, the rhodium catalyst is $[Rh(COD)Cl]_2$, the copper catalyst is $Cu(CH_3CN)_4PF_6$, and the alkaline reagent is potassium phosphate; and the rhodium catalyst ligand has a structure shown below:

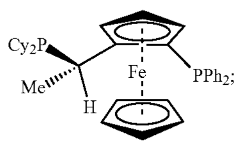

and the copper catalyst ligand has a structure shown below:

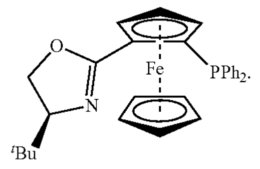

In some embodiments, an amount of substance of the $[Rh(COD)Cl]_2$ accounts for 1% to 20% of an amount of substance of the compound 1, an amount of substance of the rhodium catalyst ligand accounts for 1% to 10% of the amount of substance of the compound 1; an amount of substance of the $Cu(CH_3CN)_4PF_6$ accounts for 1% to 10% of the amount of substance of the compound 1, and an amount of substance of the copper catalyst ligand accounts for 1% to 20% of the amount of substance of the compound 1; and a molar ratio of the alkaline reagent to the compound 1 is in a range of 1:1 to 5:1.

In some embodiments, a molar ratio of the compound 1 to the 3-chlorobut-1-ene is in a range of 1:1 to 1:4.

In some embodiments, the asymmetric allylation is conducted in the presence of an organic solvent, and a dosage ratio of the organic solvent to the compound 1 is in a range of 2 mL:1 mmol to 10 mL:1 mmol.

In some embodiments, the asymmetric allylation is conducted at a temperature of −10° C. to 25° C. for 12 h to 48 h.

In some embodiments, after the asymmetric allylation is completed, the method further includes the following steps: adding water into a resulting product system to quench the asymmetric allylation, subjecting a resulting material to extraction to collect an organic phase, removing the organic solvent from the organic phase to obtain a crude product, and subjecting the crude product to separation by column chromatography to obtain the intermediate A of the (2S,3R,4R)-4,5-DHile derivative.

In some embodiments, the imine hydrolysis is conducted in the presence of hydrochloric acid, the hydrochloric acid has a concentration of 1 mol/L to 12 mol/L, and a dosage ratio of the hydrochloric acid to the intermediate A of the (2S,3R,4R)-4,5-DHile derivative is in a range of 1 L:1 mol to 5 L:1 mol; and the imine hydrolysis is conducted in the presence of an organic solvent, and a dosage ratio of the organic solvent to the intermediate A of the (2S,3R,4R)-4,5-DHile derivative is in a range of 1 L:1 mol to 4 L:1 mol.

In some embodiments, the imine hydrolysis is conducted at a temperature of 0° C. to 50° C. for 10 min to 40 min.

In some embodiments, a raw material for the Fmoc protection includes N-(9-fluorenylmethoxycarbonyloxy) succinimide (Fmoc-OSu). Based on a dosage of the intermediate A of the (2S,3R,4R)-4,5-DHile derivative, a molar ratio of the intermediate A of the (2S,3R,4R)-4,5-DHile derivative to the Fmoc-OSu is in a range of 1:1 to 1:2;

the Fmoc protection is conducted in the presence of a sodium carbonate solution, and the sodium carbonate solution has a concentration of 5 wt % to 50 wt %. Based on the dosage of the intermediate A of the (2S,3R,4R)-4,5-DHile derivative, a molar ratio of the intermediate A of the (2S,3R,4R)-4,5-DHile derivative to sodium carbonate in the sodium carbonate solution is in a range of 1:1 to 1:3; and the Fmoc protection is conducted in the presence of an organic solvent. Based on the dosage of the intermediate A of the (2S,3R,4R)-4,5-DHile derivative, a dosage ratio of the intermediate A of the (2S,3R,4R)-4,5-DHile derivative to the organic solvent for the Fmoc protection is in a range of 1 mol:1 L to 1 mol:5 L.

In some embodiments, the Fmoc protection is conducted at a temperature of 0° C. to 50° C. for 1 h to 24 h.

In some embodiments, after the Fmoc protection is completed, the method further includes the following steps: adding hydrochloric acid into a resulting product system to adjust a pH value of the product system to 7, subjecting a resulting material to extraction to collect an organic phase, removing the organic solvent from the organic phase to obtain a crude product, and subjecting the crude product to separation by column chromatography to obtain the intermediate A' of the (2S,3R,4R)-4,5-DHile derivative.

In some embodiments, the asymmetric dihydroxylation is conducted in the presence of N-methylmorpholine oxide (NMO), potassium osmate(VI) dihydrate, and AD-mix-β (Hydroquinidine 1,4-phthalazinediyl diether, $(DHQD)_2PHAL$, CAS: 140853-10-7); and a molar ratio of the intermediate A of the (2S,3R,4R)-4,5-DHile derivative, the NMO, the potassium osmate(VI) dihydrate, and the AD-mix-β is in a range of 1:(1-5):(0.001-0.1):(0.001-0.1); and the asymmetric dihydroxylation is conducted in the presence of water and an organic solvent; and a dosage ratio of the water, the organic solvent, and the intermediate A of the (2S,3R,4R)-4,5-DHile derivative is in a range of (1-3) L:(1-3) L:1 mol.

In some embodiments, the asymmetric dihydroxylation is conducted at a temperature of 0° C. to 50° C. for 1 h to 24 h.

In some embodiments, after the asymmetric dihydroxylation is completed, the method further includes the following steps: adding a $Na_2SO_3$ solution into a resulting product system to quench the asymmetric dihydroxylation, subjecting a resulting material to extraction to collect an organic phase, subjecting the organic phase to washing and drying in sequence, removing the organic solvent from the organic phase to obtain a crude product, and subjecting the crude product to separation by column chromatography to obtain the intermediate B of the (2S,3R,4R)-4,5-DHile derivative.

In some embodiments, a raw material for the acetylation includes acetyl chloride. A molar ratio of the intermediate C of the (2S,3R,4R)-4,5-DHile derivative to the acetyl chloride is in a range of 1:1 to 1:10;

the acetylation is conducted in the presence of pyridine, and a molar ratio of the intermediate C of the (2S,3R,4R)-4,5-DHile derivative to the pyridine is in a range of 1:1 to 1:10; and the acetylation is conducted in the presence of an organic solvent, and a dosage ratio of the intermediate C of the (2S,3R,4R)-4,5-DHile derivative to the organic solvent is in a range of 5 mL:1 mmol to 50 mL:1 mmol.

In some embodiments, the acetylation includes a first-stage reaction and a second-stage reaction in sequence; the first-stage reaction is conducted at a temperature of −10° C. to 10° C. for 0.5 h to 2 h; and the second-stage reaction is conducted at a temperature of 25° C. to 50° C. for 0.5 h to 2 h.

In some embodiments, after the acetylation is completed, the method further includes the following steps: washing a resulting product system with a saturated $NH_4Cl$ solution, collecting a resulting organic phase, removing the organic solvent from the organic phase to obtain a crude product, and subjecting the crude product to separation by column chromatography to obtain the intermediate D of the (2S,3R,4R)-4,5-DHile derivative.

In some embodiments, the tert-butyl ester hydrolysis is conducted in the presence of trifluoroacetic acid (TFA), and a dosage ratio of the intermediate D of the (2S,3R,4R)-4,5-DHile derivative to the TFA is in a range of 4 mmol:1 mL to 4 mmol:10 mL.

In some embodiments, the tert-butyl ester hydrolysis is conducted at a temperature of 0° C. to 50° C. for 1 h to 4 h.

In some embodiments, after the tert-butyl ester hydrolysis is completed, the method further includes the following steps: removing the organic solvent from a resulting product system to obtain a crude product, and subjecting the crude product to separation by column chromatography to obtain the (2S,3R,4R)-4,5-DHile derivative.

The present disclosure further provides an intermediate for synthesizing a (2S,3R,4R)-4,5-DHile derivative, where the intermediate is a compound having a structure shown in Formula 3:

Formula 3

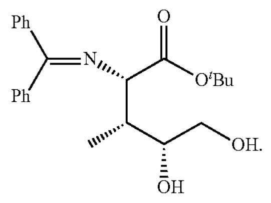

Beneficial Technical Effects

In the present disclosure, methods for preparing a series of intermediates for the (2S,3R,4R)-4,5-DHile derivative are provided, on the basis of which the (2S,3R,4R)-4,5-DHile derivative could be prepared, with a high optical purity and a low production cost. Specifically, a glycine derivative, benzophenone imine glycine tert-butyl ester (compound 1) that is easy to be purchased through commercial channels and has a low price, is selected as a starting reaction raw material; and the starting reaction raw material is subjected to asymmetric allylation, asymmetric dihydroxylation, and introduction or removal of protective groups to achieve efficient asymmetric synthesis of the (2S,3R,4R)-4,5-DHile derivative. The target product shows a desirable optical purity and a high yield. the methods have convenient operations, and are easy for large-scale production.

DETAILED DESCRIPTION OF THE EMBODIMENTS

The present disclosure provides a method for preparing an intermediate A of a (2S,3R,4R)-4,5-DHile derivative, including the following steps:

subjecting a compound 1 to asymmetric allylation to obtain the intermediate A of the (2S,3R,4R)-4,5-DHile derivative;

where the compound 1 has a structure shown in Formula 1, and the intermediate A of the (2S,3R,4R)-4,5-DHile derivative has a structure shown in Formula 2:

Formula 1

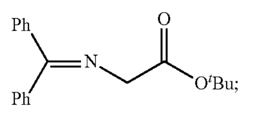

Formula 2

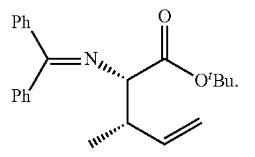

In the present disclosure, unless otherwise specified, all raw materials required for preparation are commercially available products well known to those skilled in the art.

In the present disclosure, a compound 1 is subjected to asymmetric allylation to obtain the intermediate A of the (2S,3R,4R)-4,5-DHile derivative. In some embodiments, a raw material for the asymmetric allylation includes 3-chlorobut-1-ene. In some embodiments, a molar ratio of the compound 1 to the 3-chlorobut-1-ene is in a range of 1:1 to 1:4, and preferably 1:1.2. In some embodiments, the asymmetric allylation is conducted in the presence of a rhodium catalyst, a rhodium catalyst ligand, a copper catalyst, a copper catalyst ligand, and an alkaline reagent. In some embodiments, the alkaline reagent is potassium phosphate, and a molar ratio of the alkaline reagent to the compound 1 is in a range of 1:1 to 5:1, and preferably 3:1.

In the present disclosure, in some embodiments, the rhodium catalyst is $[Rh(COD)Cl]_2$, and an amount of substance of the rhodium catalyst accounts for 1% to 20%, and preferably 1% of an amount of substance of the compound 1. In some embodiments, the rhodium catalyst ligand is (R,Sp)-L1, and an amount of substance of the rhodium catalyst ligand accounts for 1% to 10%, and preferably 2% of the amount of substance of the compound 1. The (R,Sp)-L1 has a structure as shown below:

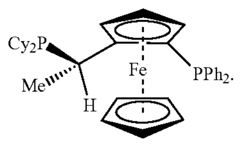

In the present disclosure, in some embodiments, the copper catalyst is $Cu(CH_3CN)_4PF_6$, and an amount of substance of the $Cu(CH_3CN)_4PF_6$ accounts for 1% to 10%, and preferably 2% of the amount of substance of the compound 1. In some embodiments, the copper catalyst ligand is (4R,2S)-L2, and an amount of substance of the copper catalyst ligand accounts for 1% to 20%, and preferably 2% of the amount of substance of the compound 1. The (4R,2S)-L2 has a structure as shown below:

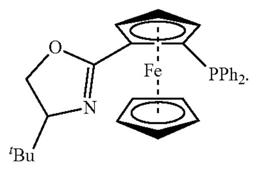

In the present disclosure, in some embodiments, the asymmetric allylation is conducted in the presence of an organic solvent. In some embodiments, the organic solvent includes one or more of tetrahydrofuran (THF), dichloromethane (DCM), and dioxane, and preferably the THF. In some embodiments, the organic solvent is used after being dried and degassed. In some embodiments, a dosage ratio of the organic solvent to the compound 1 is in a range of (2-10) mL:1 mmol, and preferably 8 mL:1 mmol.

In the present disclosure, in some embodiments, the rhodium catalyst, the rhodium catalyst ligand, and a part of the organic solvent are mixed, and a resulting mixture is subjected to complexation to obtain a rhodium catalyst slurry. The copper catalyst, the copper catalyst ligand, and the remaining organic solvent are mixed, and a resulting mixture is subjected for complexation to obtain a copper catalyst slurry. The compound 1, the alkaline reagent, and the 3-chlorobut-1-ene are added into the rhodium catalyst slurry, and then the copper catalyst slurry is added thereto, and a resulting material is subjected to asymmetric allylation. In some embodiments, the complexation for preparing the rhodium catalyst slurry and the copper catalyst slurry is conducted independently at a temperature of 0° C. to 40° C., and preferably 25° C. In some embodiments, the complexation for preparing the rhodium catalyst slurry and the copper catalyst slurry is conducted independently for less than or equal to 30 min, and preferably 15 min. In some embodiments, the asymmetric allylation is conducted at a temperature of −10° C. to 25° C., and preferably 0° C. In some embodiments, the asymmetric allylation is conducted for 12 h to 48 h, and preferably 24 h. In some embodiments, the asymmetric allylation is conducted in a closed environment. In some embodiments, the asymmetric allylation is conducted under stirring.

In the present disclosure, in some embodiments, after the asymmetric allylation is completed, the method further includes the following steps: adding water into a resulting product system to quench the asymmetric allylation, subjecting a resulting material to extraction to collect an organic phase, removing the organic solvent from the organic phase to obtain a crude product, and subjecting the crude product to separation by column chromatography to obtain the intermediate A of the (2S,3R,4R)-4,5-DHile derivative. In some embodiments, an extractant used in the extraction is ethyl acetate. In some embodiments, after the extraction, the organic phase is subjected to drying, and a desiccant used in the drying is anhydrous sodium sulfate. In some embodiments, after the drying, a resulting material is subjected to filtration, and then, a resulting filtrate is subjected to removal of the organic solvent to obtain the crude product. In some embodiments, removal of the organic solvent is performed by vacuum distillation, and the organic solvent can be recycled. In some embodiments, a silica gel for the separation is 200-300 mesh silica gel. In some embodiments, an eluent for the separation is a mixture of petroleum ether and ethyl acetate, and a volume ratio of the petroleum ether to the ethyl acetate in the eluent is 99:1.

Further provided is a method for preparing an intermediate A' of a (2S,3R,4R)-4,5-DHile derivative, including the following steps:

preparing the intermediate A of the (2S,3R,4R)-4,5-DHile derivative by the method described above; and subjecting the intermediate A of the (2S,3R,4R)-4,5-DHile derivative to imine hydrolysis and Fmoc protection to obtain the intermediate A' of the (2S,3R,4R)-4,5-DHile derivative;

where the intermediate A' of the (2S,3R,4R)-4,5-DHile derivative has a structure shown in Formula 2':

Formula 2'

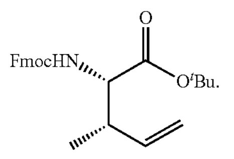

In the present disclosure, the intermediate A of the (2S,3R,4R)-4,5-DHile derivative is converted into the intermediate A' of the (2S,3R,4R)-4,5-DHile derivative, which is convenient for separation by high-performance liquid chromatography (HPLC) to determine the enantioselectivity. Moreover, the intermediate A' of the (2S,3R,4R)-4,5-DHile derivative can be used to directly prepare the intermediate C of the (2S,3R,4R)-4,5-DHile derivative, which will be described in detail later.

In the present disclosure, in some embodiments, the method for preparing the intermediate A of the (2S,3R,4R)-4,5-DHile derivative is consistent with that in the above technical scheme, which will not be repeated here.

In the present disclosure, after the intermediate A of the (2S,3R,4R)-4,5-DHile derivative is obtained, the intermediate A of the (2S,3R,4R)-4,5-DHile derivative is subjected to imine hydrolysis and Fmoc protection to obtain the intermediate A' of the (2S,3R,4R)-4,5-DHile derivative. Detailed descriptions are provided below.

In the present disclosure, in some embodiments, the imine hydrolysis is conducted in the presence of hydrochloric acid. In some embodiments, the hydrochloric acid has a concentration of 1 mol/L to 12 mol/L, and preferably 1 mol/L; and a dosage ratio of the hydrochloric acid to the intermediate A of the (2S,3R,4R)-4,5-DHile derivative is in a range of (1-5) L:1 mol, and preferably (1-2) L:1 mol. In some embodiments, the imine hydrolysis is conducted in the presence of an organic solvent. In some embodiments, the organic solvent includes one or more of THF, dioxane, and methanol, and preferably the THF. In some embodiments, a dosage ratio of the organic solvent to the intermediate A of the (2S,3R,4R)-4,5-DHile derivative is in a range of (1-4) L:1 mol, and preferably 2 L:1 mol.

In the present disclosure, in some embodiments, the intermediate A of the (2S,3R,4R)-4,5-DHile derivative is dissolved in the organic solvent, and the hydrochloric acid is added dropwise under stirring to perform the imine hydrolysis. In some embodiments, the imine hydrolysis is conducted at a temperature of 0° C. to 50° C., and preferably ambient temperature. In one example, the ambient temperature is specifically 25° C. In some embodiments, the imine hydrolysis is conducted for 10 min to 40 min, and preferably 20 min. In some embodiments, TLC is conducted to monitor the reaction progress. In some embodiments, the imine hydrolysis is conducted under stirring.

In the present disclosure, in some embodiments, after the imine hydrolysis is completed, the method further includes the following steps: adding a saturated sodium carbonate solution into a resulting product system to adjust a pH value of the product system to 7 to 9 (preferably 8), subjecting a resulting material to extraction to collect an organic phase, removing the organic solvent from the organic phase to obtain a crude product, and subjecting the crude product to the Fmoc protection directly. In some embodiments, an extractant used in the extraction is ethyl acetate. In some embodiments, after the extraction, the organic phase is subjected to drying. In some embodiments, a desiccant in the drying is anhydrous sodium sulfate. After the drying, a resulting material is subjected to filtration, and then a filtrate is subjected to removal of the organic solvent to obtain the crude product. In some embodiments, the removal of the organic solvent is performed by vacuum distillation, and the organic solvent can be recycled.

In the present disclosure, a raw material for the Fmoc protection includes Fmoc-OSu. Based on a dosage of the intermediate A of the (2S,3R,4R)-4,5-DHile derivative, a molar ratio of the intermediate A of the (2S,3R,4R)-4,5-DHile derivative to the Fmoc-OSu is in a range of 1:1 to 1:2, and preferably 1:1.1. In some embodiments, the Fmoc protection is conducted in the presence of a sodium carbonate solution, and the sodium carbonate solution has a concentration of 5 wt % to 50 wt %, and preferably 10 wt %. Based on the dosage of the intermediate A of the (2S,3R,4R)-4,5-DHile derivative, a molar ratio of the intermediate A of the (2S,3R,4R)-4,5-DHile derivative to sodium carbonate in the sodium carbonate solution is in a range of 1:1 to 1:3, and preferably 1:1.5. In some embodiments, the Fmoc protection is conducted in the presence of an organic solvent, and the organic solvent is one or more of 1,4-dioxane, THF, and methanol, and preferably the 1,4-dioxane. Based on the dosage of the intermediate A of the (2S,3R,4R)-4,5-DHile derivative, a dosage ratio of the intermediate A of the (2S,3R,4R)-4,5-DHile derivative to the organic solvent for the Fmoc protection is in a range of 1 mol:1 L to 1 mol:5 L, and preferably 1 mol:2 L.

In the present disclosure, in some embodiments, after the imine hydrolysis, the crude product is dissolved in the organic solvent for the Fmoc protection, the sodium carbonate solution is added, and then the Fmoc-OSu is added dropwise to perform the Fmoc protection reaction. In some embodiments, the Fmoc protection is conducted at a temperature of 0° C. to 50° C., and preferably ambient temperature. In some embodiments, the Fmoc protection is conducted for 1 h to 24 h, and preferably 2 h. In some embodiments, the Fmoc protection is conducted under stirring.

In the present disclosure, in some embodiments, after the Fmoc protection is completed, the method further includes the following steps: adding hydrochloric acid into a resulting product system to adjust a pH value of the product system to 7, subjecting a resulting material to extraction to collect an organic phase, removing the organic solvent from the organic phase to obtain a crude product, and subjecting the crude product to separation by column chromatography to obtain the intermediate A' of the (2S,3R,4R)-4,5-DHile derivative. In some embodiments, an extractant used in the extraction is ethyl acetate. In some embodiments, after the extraction, the organic phase is subjected to drying, and a desiccant used in the drying is anhydrous sodium sulfate. In some embodiments, after the drying, a resulting material is subjected to filtration to collect a filtrate, and then, the filtrate is subjected to removal of the organic solvent to obtain the crude product. In some embodiments, the removal of the organic solvent is performed by vacuum distillation, and the organic solvent can be recycled. In some embodiments, a silica gel for the separation is 200-300 mesh silica gel. In some embodiments, an eluent for the separation is a mixture of ethyl acetate and petroleum ether, and a volume ratio of the ethyl acetate and to petroleum ether in the eluent is 15:85.

Further provided is a method for preparing an intermediate B of a (2S,3R,4R)-4,5-DHile derivative, including the following steps:

preparing the intermediate A of the (2S,3R,4R)-4,5-DHile derivative by the method described above; and subjecting the intermediate A of the (2S,3R,4R)-4,5-DHile derivative to asymmetric dihydroxylation to obtain the intermediate B of the (2S,3R,4R)-4,5-DHile derivative; where the intermediate B of the (2S,3R,4R)-4,5-DHile derivative has a structure shown in Formula 3:

Formula 3

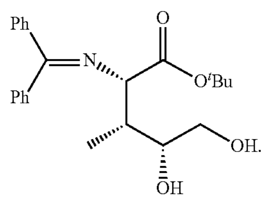

In the present disclosure, the method for preparing the intermediate A of the (2S,3R,4R)-4,5-DHile derivative is consistent with that in the above technical scheme, which will not be repeated here.

In the present disclosure, after the intermediate A of the (2S,3R,4R)-4,5-DHile derivative is obtained, the intermediate A of the (2S,3R,4R)-4,5-DHile derivative is subjected to asymmetric dihydroxylation to obtain the intermediate B of the (2S,3R,4R)-4,5-DHile derivative. In some embodiments, the asymmetric dihydroxylation is conducted in the presence of NMO, potassium osmate(VI) dihydrate ($K_2OsO_4 \cdot 2H_2O$), and AD-mix-β. In some embodiments, a molar ratio of the intermediate A of the (2S,3R,4R)-4,5-DHile derivative, the NMO, the potassium osmate(VI) dihydrate ($K_2OsO_4 \cdot 2H_2O$), and the AD-mix-β is in a range of 1:(1-5):(0.001-0.1):(0.001-0.1), and preferably 1:3:0.01:0.01. In some embodiments, the asymmetric dihydroxylation is conducted in the presence of water and an organic solvent. In some embodiments, the organic solvent includes one or more of acetone, acetonitrile, and methanol, and preferably the acetone. In some embodiments, a dosage ratio of the water, the organic solvent, and the intermediate A of the (2S,3R,4R)-4,5-DHile derivative is in a range of (1-3) L:(1-3) L:1 mol, and preferably 1 L:2 L:1 mol.

In the present disclosure, in some embodiments, the potassium osmate(VI) dihydrate, the AD-mix-β, a part of the water, and a part of the organic solvent are mixed. After the potassium osmate(VI) dihydrate and the AD-mix-β are dissolved, the NMO, the intermediate A of the (2S,3R,4R)-4,5-DHile derivative, the remaining water, and the remaining organic solvent are added, and a resulting mixture is subjected to asymmetric dihydroxylation. In some embodiments, the asymmetric dihydroxylation is conducted at a temperature of 0° C. to 50° C., and preferably ambient temperature. In some embodiments, the asymmetric dihydroxylation is conducted for 1 h to 24 h, and preferably 12 h. In some embodiments, the asymmetric dihydroxylation is conducted under stirring.

In the present disclosure, in some embodiments, after the asymmetric dihydroxylation, the method further includes the following steps: adding a $Na_2SO_3$ solution into a resulting product system to quench the asymmetric dihydroxylation, subjecting a resulting material to extraction to collect an organic phase, subjecting the organic phase to washing and drying in sequence, removing the organic solvent from the organic phase to obtain a crude product, and subjecting the crude product to separation by column chromatography to obtain the intermediate B of the (2S,3R,4R)-4,5-DHile derivative. In some embodiments, an extractant used in the extraction is ethyl acetate. In some embodiments, a reagent for the washing is a saturated sodium chloride solution. In some embodiments, a desiccant for the drying is anhydrous sodium sulfate. In some embodiments, after the drying, a resulting material is subjected to filtration to collect a filtrate, and then, the filtrate is subjected to removal of the organic solvent to obtain the crude product. In some embodiments, the removal of the organic solvent is performed by vacuum distillation, and the organic solvent can be recycled. In some embodiments, a silica gel for the separation is 200-300 mesh silica gel. In some embodiments, an eluent for the separation is a mixture of ethyl acetate and petroleum ether, and a volume ratio of the ethyl acetate to the petroleum ether in the eluent is 35:65.

Further provided is a method for preparing an intermediate C of a (2S,3R,4R)-4,5-DHile derivative, including the following steps:

preparing the intermediate B of the (2S,3R,4R)-4,5-DHile derivative by the method described above; and subjecting the intermediate B of the (2S,3R,4R)-4,5-DHile derivative to imine hydrolysis and Fmoc protection to obtain the intermediate C of the (2S,3R,4R)-4,5-DHile derivative;

where the intermediate C of the (2S,3R,4R)-4,5-DHile derivative has a structure shown in Formula 4:

Formula 4

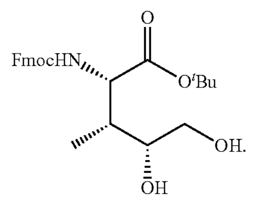

In the present disclosure, in some embodiments, the method for preparing the intermediate A of the (2S,3R,4R)-4,5-DHile derivative and the intermediate B of the (2S,3R,4R)-4,5-DHile derivative is consistent with that in the above technical scheme, which will not be repeated here.

In the present disclosure, after the intermediate B of the (2S,3R,4R)-4,5-DHile derivative is obtained, the intermediate B of the (2S,3R,4R)-4,5-DHile derivative is subjected to imine hydrolysis and Fmoc protection to obtain the intermediate C of the (2S,3R,4R)-4,5-DHile derivative. In some embodiments, the raw materials, reagents, reaction conditions, and post-treatment methods required for the imine hydrolysis and the Fmoc protection are similar to those in the above technical solution, and will not be repeated here.

Further provided is a method for preparing an intermediate C of a (2S,3R,4R)-4,5-DHile derivative, including the following steps:

preparing the intermediate A' of the (2S,3R,4R)-4,5-DHile derivative by the method described above; and subjecting the intermediate A' of the (2S,3R,4R)-4,5-DHile derivative to asymmetric dihydroxylation to obtain the intermediate C of the (2S,3R,4R)-4,5-DHile derivative; where the intermediate C of the (2S,3R,4R)-4,5-DHile derivative has a structure shown in Formula 4:

Formula 4

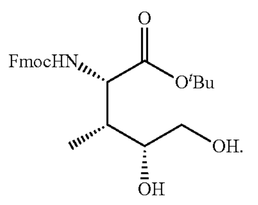

In the present disclosure, in some embodiments, the method for preparing the intermediate A of the (2S,3R,4R)-4,5-DHile derivative and the intermediate A' of the (2S,3R,4R)-4,5-DHile derivative is consistent with that in the above technical scheme, which will not be repeated here.

In the present disclosure, after the intermediate A' of the (2S,3R,4R)-4,5-DHile derivative is obtained, the intermediate A' of the (2S,3R,4R)-4,5-DHile derivative is subjected to asymmetric dihydroxylation to obtain the intermediate C of the (2S,3R,4R)-4,5-DHile derivative. In some embodiments, the raw materials, reagents, reaction conditions, and post-treatment methods required for the asymmetric dihydroxylation are consistent to those in the above technical solutions, and will not be repeated here.

Further provided is a method for preparing a (2S,3R,4R)-4,5-DHile derivative, including the following steps:

subjecting a compound 1 to asymmetric allylation to obtain an intermediate A of the (2S,3R,4R)-4,5-DHile derivative;

subjecting the intermediate A of the (2S,3R,4R)-4,5-DHile derivative to asymmetric dihydroxylation to obtain an intermediate B of the (2S,3R,4R)-4,5-DHile derivative;

subjecting the intermediate B of the (2S,3R,4R)-4,5-DHile derivative to imine hydrolysis and Fmoc protection to obtain an intermediate C of the (2S,3R,4R)-4,5-DHile derivative;

subjecting the intermediate C of the (2S,3R,4R)-4,5-DHile derivative to acetylation to obtain an intermediate D of the (2S,3R,4R)-4,5-DHile derivative; and subjecting the intermediate D of the (2S,3R,4R)-4,5-DHile derivative to tert-butyl ester hydrolysis to obtain the (2S,3R,4R)-4,5-DHile derivative;

where the compound 1, the intermediate A of the (2S,3R,4R)-4,5-DHile derivative, the intermediate B of the (2S,3R,4R)-4,5-DHile derivative, the intermediate C of the (2S,3R,4R)-4,5-DHile derivative, the intermediate D of the (2S,3R,4R)-4,5-DHile derivative, and the (2S,3R,4R)-4,5-DHile derivative have structures shown in Formula 1, Formula 2, Formula 3, Formula 4, Formula 5, and Formula 6, respectively:

Formula 1

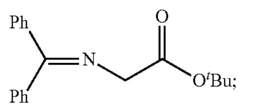

Formula 2

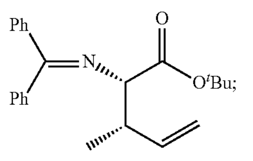

-continued

Formula 3

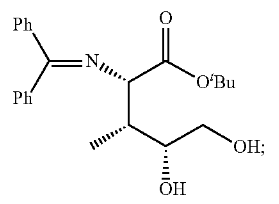

Formula 4

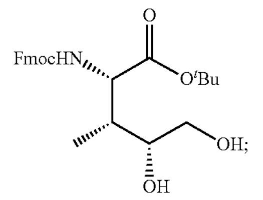

Formula 5

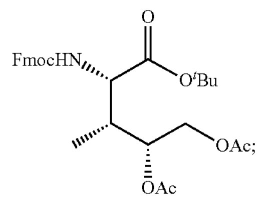

Formula 6

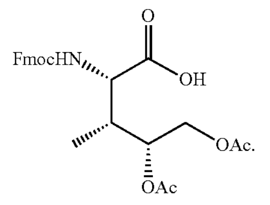

In the present disclosure, in some embodiments, the method for preparing the intermediate A of the (2S,3R,4R)-4,5-DHile derivative, the intermediate B of the (2S,3R,4R)-4,5-DHile derivative, and the intermediate C of the (2S,3R,4R)-4,5-DHile derivative is consistent with that in the above technical scheme, which will not be repeated here.

In the present disclosure, in some embodiments, after the intermediate C of the (2S,3R,4R)-4,5-DHile derivative is obtained, the intermediate C of the (2S,3R,4R)-4,5-DHile derivative is subjected to acetylation to obtain the intermediate D of the (2S,3R,4R)-4,5-DHile derivative. In some embodiments, a raw material for the acetylation includes acetyl chloride, and a molar ratio of the intermediate C of the (2S,3R,4R)-4,5-DHile derivative to the acetyl chloride is in a range of 1:1 to 1:10, and preferably 1:2.2. In some embodiments, the acetylation is conducted in the presence of pyridine, and a molar ratio of the intermediate C of the (2S,3R,4R)-4,5-DHile derivative to the pyridine is in a range of 1:1 to 1:10, and preferably 1:1.5. In some embodiments, the acetylation is conducted in the presence of an organic solvent. In some embodiments, the organic solvent includes one or more of DCM, ethyl acetate, and methanol, and preferably the DCM. In some embodiments, the organic solvent is used after drying. In some embodiments, a dosage ratio of the intermediate C of the (2S,3R,4R)-4,5-DHile derivative to the organic solvent is in a range of 5 mL:1 mmol to 50 mL:1 mmol, and preferably 10 mL:1 mmol.

In the present disclosure, in some embodiments, the intermediate C of the (2S,3R,4R)-4,5-DHile derivative, the pyridine, and the organic solvent are mixed, and then the acetyl chloride is added dropwise, and a resulting material is subjected to the acetylation. In some embodiments, the acetylation includes a first-stage reaction and a second-stage reaction in sequence. In some embodiments, the first-stage reaction is conducted at a temperature of −10° C. to 10° C., and preferably 0° C. In some embodiments, the first-stage reaction is conducted for 0.5 h to 2 h, and preferably 1 h. In some embodiments, the first-stage reaction starts time when the dropwise addition of acetyl chloride is completed. In some embodiments, the second-stage reaction is conducted at a temperature of 0° C. to 50° C., and preferably ambient temperature. In some embodiments, the second-stage reaction is conducted for 0.5 h to 2 h, and preferably 1 h. In some embodiments, the acetylation is conducted under stirring.

In the present disclosure, in some embodiments, after the acetylation is completed, the method further includes the following steps: washing a resulting product system with a saturated $NH_4Cl$ solution and collecting a resulting organic phase, removing the organic solvent from the organic phase to obtain a crude product, and subjecting the crude product to separation by column chromatography to obtain the intermediate D of the (2S,3R,4R)-4,5-DHile derivative. In some embodiments, after the organic phase is collected, the organic phase is subjected to drying, and a desiccant for the drying is anhydrous sodium sulfate. In some embodiments, after the drying, a resulting material is subjected to filtration to collect a filtrate, and then, the filtrate is subjected to removal of the organic solvent to obtain the crude product. In some embodiments, the removal of the organic solvent is performed by vacuum distillation, and the organic solvent can be recycled. In some embodiments, a silica gel for the separation is 200-300 mesh silica gel. In some embodiments, an eluent for the separation is a mixture of ethyl acetate and petroleum ether, and a volume ratio of the ethyl acetate to the petroleum ether in the eluent is 8:92.

In the present disclosure, after the intermediate D of the (2S,3R,4R)-4,5-DHile derivative is obtained, the intermediate D of the (2S,3R,4R)-4,5-DHile derivative is subjected to tert-butyl ester hydrolysis to obtain the (2S,3R,4R)-4,5-DHile derivative. In some embodiments, the tert-butyl ester hydrolysis is conducted in the presence of TFA, and a dosage ratio of the intermediate D of the (2S,3R,4R)-4,5-DHile derivative to the TFA is in a range of 4 mmol:(1-10) mL, and preferably 4 mmol:5 mL.

In the present disclosure, in some embodiments, the intermediate D of the (2S,3R,4R)-4,5-DHile derivative is mixed with the TFA, and a resulting material is subjected to the tert-butyl ester hydrolysis. In some embodiments, the tert-butyl ester hydrolysis is conducted at a temperature of 0° C. to 50° C., and preferably ambient temperature. In some embodiments, the tert-butyl ester hydrolysis is conducted for 1 h to 4 h, and preferably 2 h. In some embodiments, TLC is conducted to monitor the reaction progress. In some embodiments, the tert-butyl ester hydrolysis is conducted under stirring.

In the present disclosure, in some embodiments, after the tert-butyl ester hydrolysis is completed, the method further includes the following steps: removing the organic solvent from a resulting product system to obtain a crude product, and subjecting the crude product to separation by column chromatography to obtain the (2S,3R,4R)-4,5-DHile derivative. In some embodiments, a process for removing the organic solvent is vacuum distillation, and the solvent can be recycled. In some embodiments, a silica gel for the separation is 200-300 mesh silica gel. In some embodiments, an eluent for the separation is a mixture of methanol and DCM, and a volume ratio of the methanol to the DCM in the eluent is 5:95.

Further provided is a method for preparing a (2S,3R,4R)-4,5-DHile derivative, including the following steps:

subjecting a compound 1 to asymmetric allylation to obtain an intermediate A of the (2S,3R,4R)-4,5-DHile derivative;

subjecting the intermediate A of the (2S,3R,4R)-4,5-DHile derivative to imine hydrolysis and 9-fluorenylmethoxycarbonyl (Fmoc) protection to obtain an intermediate A' of the (2S,3R,4R)-4,5-DHile derivative;

subjecting the intermediate A' of the (2S,3R,4R)-4,5-DHile derivative to asymmetric dihydroxylation to obtain an intermediate C of the (2S,3R,4R)-4,5-DHile derivative;

subjecting the intermediate C of the (2S,3R,4R)-4,5-DHile derivative to acetylation to obtain an intermediate D of the (2S,3R,4R)-4,5-DHile derivative; and subjecting the intermediate D of the (2S,3R,4R)-4,5-DHile derivative to tert-butyl ester hydrolysis to obtain the (2S,3R,4R)-4,5-DHile derivative;

where the compound 1, the intermediate A of the (2S,3R,4R)-4,5-DHile derivative, the intermediate A' the (2S,3R,4R)-4,5-DHile derivative, the intermediate C of the (2S,3R,4R)-4,5-DHile derivative, the intermediate D of the (2S,3R,4R)-4,5-DHile derivative, and the (2S,3R,4R)-4,5-DHile derivative have structures shown in Formula 1, Formula 2, Formula 2', Formula 4, Formula 5, and Formula 6, respectively:

Formula 1

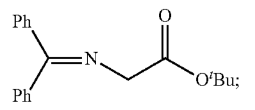

Formula 2

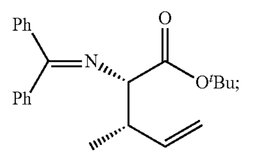

Formula 2'

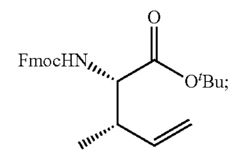

Formula 4

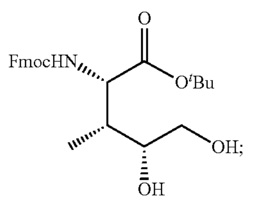

Formula 5

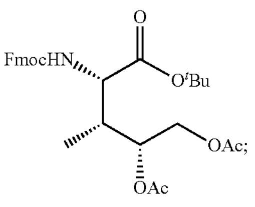

-continued

Formula 6

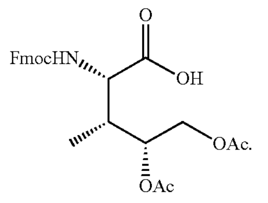

In the present disclosure, in some embodiments, the method of the intermediate A of the (2S,3R,4R)-4,5-DHile derivative and the intermediate A' of the (2S,3R,4R)-4,5-DHile derivative is consistent with that in the above technical scheme, which will not be repeated here.

In the present disclosure, after the intermediate A' of the (2S,3R,4R)-4,5-DHile derivative is obtained, the intermediate A' of the (2S,3R,4R)-4,5-DHile derivative is subjected to asymmetric dihydroxylation to obtain the intermediate C of the (2S,3R,4R)-4,5-DHile derivative. In some embodiments, the raw materials, reagents, reaction conditions, and post-treatment methods required for the asymmetric dihydroxylation are consistent to those in the above technical solution, and will not be repeated here.

In the present disclosure, after the intermediate C of the (2S,3R,4R)-4,5-DHile derivative is obtained, the method for preparing the intermediate D of the (2S,3R,4R)-4,5-DHile derivative and the (2S,3R,4R)-4,5-DHile derivative is consistent with that in the above technical scheme, which will not be repeated here.

Further provided is an intermediate for synthesizing the (2S,3R,4R)-4,5-DHile derivative above, where the intermediate is a compound having a structure shown in Formula 3:

Formula 3

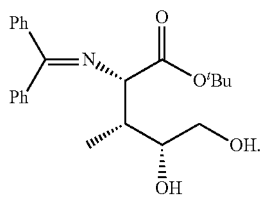

The technical solutions of the present disclosure will be clearly and completely described below with reference to the examples of the present disclosure. Apparently, the described examples are merely a part rather than all of the examples of the present disclosure. All other examples obtained by those skilled in the art based on the examples of the present disclosure without creative efforts shall fall within the scope of the present disclosure.

Example 1 Synthesis of Compound 2

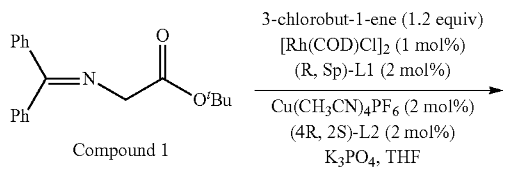

Compound 1

-continued

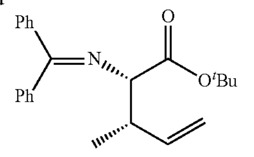

Compound 2

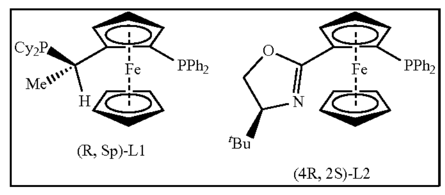

(R, Sp)-L1

(4R, 2S)-L2

Under nitrogen protection, $[Rh(COD)Cl]_2$ (50 mg, 1 mol %), (R,Sp)-L1 (120 mg, 2 mol %), and dried and degassed THF (40 mL) were mixed, and a resulting mixture was stirred at 25° C. for 15 min to obtain a rhodium catalyst slurry. $Cu(CH_3CN)_4PF_6$ (70 mg, 2 mol %) and (4R,2S)-L2 (120 mg, 2 mol %) were mixed with dried and degassed THF (40 mL), and a resulting mixture was stirred at 25° C. for 15 min to obtain a copper catalyst slurry. Compound 1 (3 g, 10 mmol), $K_3PO_4$ (3.6 g, 15 mmol), and 3-chlorobut-1-ene (1.08 g, 12 mmol) were added into the rhodium catalyst slurry, and then the copper catalyst slurry was added thereto. A resulting mixture was subjected to reaction by stirring at 0° C. for 24 h under sealed conditions. After the reaction, 100 mL of water was added to a resulting product system to quench the reaction, and 300 mL of ethyl acetate was added, and a resulting material was subjected to extraction 3 times. Resulting organic phases were combined, dried over anhydrous sodium sulfate, and filtered to obtain a filtrate. The filtrate was subjected to vacuum distillation, and a solvent was recovered, obtaining a crude product. The crude product was subjected to separation and purification by silica gel column chromatography (using 200-300 mesh silica gel and a mixed solvent of petroleum ether and ethyl acetate with a volume ratio of 99:1 as an eluent) to obtain 3.35 g of a colorless oily liquid, namely the compound 2, with a yield of 96%.

The chemical name of the compound 2 was (2S,3S)-2-((diphenylmethylene)amino)-3-methylpent-4-tert-butyl enoate, and NMR data thereof were as follows:

$^1H$ NMR (600 MHz, $CDCl_3$) δ 7.68-7.65 (m, 2H), 7.44-7.41 (m, 3H), 7.38 (ddd, J=6.5, 3.8, 1.2 Hz, 1H), 7.32 (dd, J=10.3, 4.6 Hz, 2H), 7.16-7.13 (m, 2H), 5.69 (ddd, J=17.6, 10.3, 7.6 Hz, 1H), 5.06-5.02 (m, 1H), 4.97-4.94 (m, 1H), 3.86-3.80 (m, 1H), 2.95-2.88 (m, 1H), 1.44 (s, 9H), 1.10 (d, J=6.8 Hz, 3H). $^{13}C$ NMR (151 MHz, $CDCl_3$) δ 170.7, 170.3, 140.9, 139.9, 136.9, 130.3, 128.9, 128.6, 128.5, 128.1, 128.1, 114.8, 81.1, 70.8, 41.8, 28.2, 15.9. HRMS (ESI+) calcd (calculated). for $C_{23}H_{28}NO_2$ $(M+H)^+$: 350.2115; found: 350.2129.

Example 2 Synthesis of Compound 2'

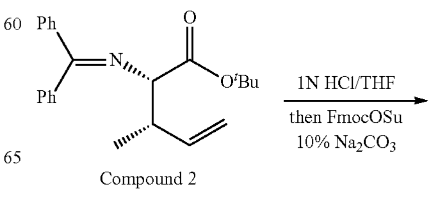

Compound 2

-continued

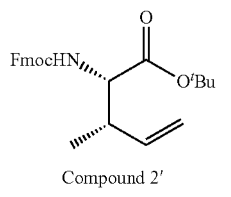

Compound 2'

The compound 2 (34 g) was dissolved in THF (200 mL), and hydrochloric acid (1 mol/L, 100 mL) was added dropwise under stirring, a resulting mixture was stirred at ambient temperature (25° C.) for 20 min, and the compound 2 was monitored by TLC until the reaction was complete. After the reaction was completed, a saturated sodium carbonate solution was added to a resulting product system until a pH value of the system reached 8, and then ethyl acetate was added, and a resulting material was subjected to extraction 3 times. Resulting organic phases were combined, dried over anhydrous sodium sulfate, and filtered to obtain a filtrate. The filtrate was subjected to vacuum distillation, and a solvent was recovered obtaining a remaining material was a crude product.

The crude product was dissolved in 1,4-dioxane (200 mL), and a 10 wt % aqueous solution of sodium carbonate (21 g, 0.15 mol) was added, and then Fmoc-Osu (37 g, 0.11 mol) was added dropwise, and then, a resulting material was subjected to a reaction by stirring at ambient temperature for 2 h. After the reaction was completed, hydrochloric acid (2 mol/L) was added to a resulting product system until a pH value of the system was 7. Then, a resulting material was subjected to extraction 3 times with 500 mL of ethyl acetate to collect organic phases. The organic phases were combined, washed with saturated sodium chloride solution, dried over anhydrous sodium sulfate, and filtered to collect a filtrate. The filtrate was subjected to vacuum distillation, and a solvent was recovered, obtaining a crude product. The crude product was subjected to separation and purification by silica gel column chromatography (using 200-300 mesh silica gel and a mixed solvent of ethyl acetate and petroleum ether with a volume ratio of 15:85 as an eluent) to obtain 3.13 g of a colorless oily liquid, namely the compound 2', with a yield of 78%.

The compound 2' was subjected to HPLC analysis to determine the enantioselectivity, and the results are shown in Tables 1 and 2. The conditions of the HPLC analysis were as follows: DAICEL CHIRALPAK IC; a mobile phase was n-hexane and isopropanol, and a volume ratio of the n-hexane to isopropanol was 95:5; a detection wavelength was 254 nm, and a flow rate of the mobile phase was 1.0 mL/min; $tR_1$=11.353 min (minor), $tR_2$=12.350 min (minor), $tR_3$=13.032 min (major), $tR_4$=14.610 min (minor). The results show that the dr value is 12:1 and the enantiomeric excess (ee) value is 99%.

TABLE 1

HPLC analysis data corresponding to racemic product of compound 2'

| Peak | Retention time (min) | Area (mAU × min) | Height (mAU) | Area (%) |
|---|---|---|---|---|
| 1 | 11.958 | 11.056 | 36.803 | 33.50 |
| 2 | 12.820 | 5.419 | 16.809 | 16.42 |
| 3 | 13.540 | 11.177 | 34.990 | 33.86 |
| 4 | 14.983 | 5.354 | 14.341 | 16.22 |

TABLE 2

HPLC analysis data corresponding to chiral product of compound 2'

| Peak | Retention time (min) | Area (mAU × min) | Height (mAU) | Area (%) |
|---|---|---|---|---|
| 1 | 11.353 | 0.038 | 0.098 | 0.17 |
| 2 | 12.350 | 1.648 | 4.651 | 7.50 |
| 3 | 13.032 | 17.741 | 46.786 | 80.70 |
| 4 | 14.610 | 2.556 | 6.321 | 11.63 |

The optical rotation data of the compound 2' was: $[\alpha]^{25}_{D}$=−5.8 (c 0.5, $CH_2Cl_2$); and NMR data thereof were as follows:

$^1$H NMR (600 MHz, $CDCl_3$) δ 7.77 (d, J=7.6 Hz, 2H), 7.61 (d, J=7.5 Hz, 2H), 7.40 (d, J=7.5 Hz, 2H), 7.32 (d, J=7.4 Hz, 2H), 5.79 (dt, J=17.4, 8.7 Hz, 1H), 5.39 (d, J=8.7 Hz, 1H), 5.12 (d, J=4.0 Hz, 1H), 5.10 (s, 1H), 4.42 (q, J=10.1 Hz, 1H), 4.39-4.34 (m, 1H), 4.33 (dd, J=8.8, 4.6 Hz, 1H), 4.24 (t, J=7.2 Hz, 1H), 2.70 (d, J=6.0 Hz, 1H), 1.50 (s, 9H), 1.10 (d, J=6.9 Hz, 3H). $^{13}$C NMR (151 MHz, $CDCl_3$) δ 170.5, 156.0, 144.1, 143.9, 141.4, 138.9, 127.8, 127.14, 125.3, 125.2, 120.1, 116.1, 82.4, 67.1, 58.2, 47.3, 41.1, 28.2, 15.4. HRMS (ESI+) calcd. for $C_{25}H_{29}NNaO_4^+$ $(M+Na)^+$: 430.1989; found: 430.2008.

Example 3 Synthesis of Compound 3

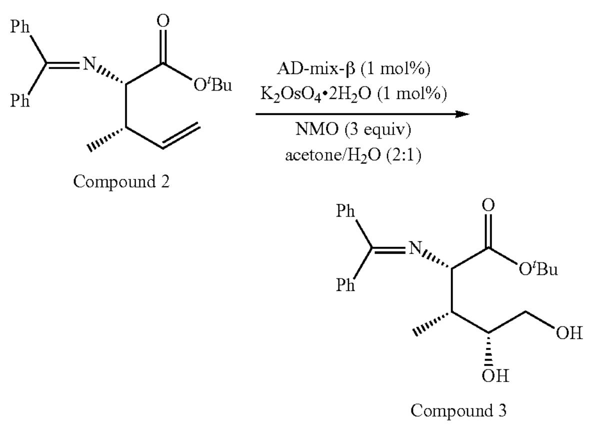

Compound 2

Compound 3

$K_2OsO_4$·$2H_2O$ (370 mg, 1 mol %), AD-mix-β (780 mg, 1 mol %), and 100 mL of acetone aqueous solution (a volume ratio of acetone to water was 2:1) were mixed and stirred for 10 min, followed by adding NMO (35.1 g, 0.3 mol), the compound 2 (35.0 g, 0.1 mol), and 300 mL of acetone aqueous solution (a volume ratio of acetone to water was 2:1). A resulting material was subjected to a reaction by stirring at ambient temperature for 12 h. After the reaction was completed, an excess of saturated $Na_2SO_3$ solution was added to quench the reaction, and 500 mL of ethyl acetate was added. A resulting material was subjected to extraction 3 times to collect organic phases. The organic phases were combined, washed with saturated sodium chloride solution, dried over anhydrous sodium sulfate, and filtered to collect a filtrate. The filtrate was subjected to vacuum distillation, and a solvent was recovered, obtaining a crude product. The crude product was subjected to separation and purification by silica gel column chromatography (using 200-300 mesh silica gel and a mixed solvent of ethyl acetate and petroleum ether in a volume ratio of 35:65 as an eluent) to obtain 3.06 g of a light yellow oily liquid, namely the compound 3, with a yield of 80%.

The chemical name of the compound 3 was (2S,3R,4R)-2-((diphenylmethylene)amino)-4,5-dihydroxy-3-tert-butyl methylvalerate, and NMR data thereof were as follows:

$^1$H NMR (600 MHz, $CDCl_3$) δ 7.59 (d, J=7.8 Hz, 2H), 7.44 (d, J=1.9 Hz, 3H), 7.40 (t, J=7.1 Hz, 1H), 7.33 (t, J=7.5 Hz, 2H), 7.16 (d, J=3.1 Hz, 2H), 4.16 (d, J=3.2 Hz, 1H), 3.79 (dd, J=8.0, 3.8 Hz, 1H), 3.77-3.69 (m, 1H), 3.54 (dd, J=11.2, 5.2 Hz, 1H), 2.20-2.12 (m, 1H), 1.43 (d, J=6.4 Hz, 9H), 1.05 (d, J=7.0 Hz, 3H). $^{13}$C NMR (151 MHz, $CDCl_3$) δ 170.72, 170.34, 139.01, 135.90, 130.89, 129.04, 128.91, 128.70, 128.34, 127.66, 81.64, 74.49, 69.19, 65.05, 39.86, 28.18, 13.95. HRMS (ESI+) calcd. for $C_{23}H_{30}NO_4^+$ $(M+H)^+$: 384.2169; found: 384.2178.

Example 3

Compound 4 was Synthesized Using the Compound 3:

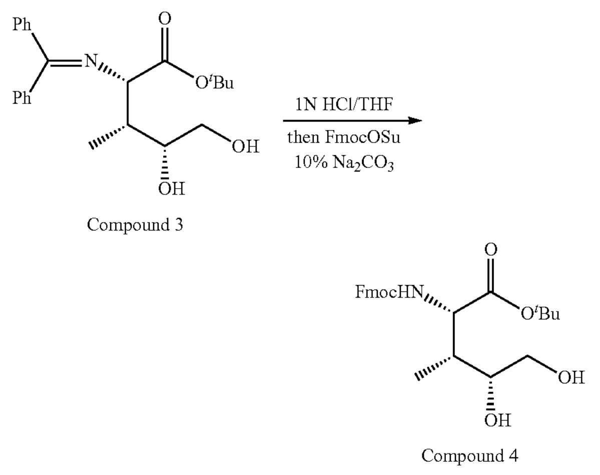

Compound 3
Compound 4

The compound 3 (19.15 g, 50 mmol) was dissolved in THF (200 mL), and hydrochloric acid (1 mol/L, 100 mL) was added dropwise under stirring, a resulting mixture was subjected to a reaction by stirring at ambient temperature for 20 min, and the compound 3 was monitored by TLC until the reaction was complete. After the reaction was completed, a saturated sodium carbonate solution was added to a resulting product system until a pH value of the system reached 7. Then, a resulting material was subjected to extraction 3 times with ethyl acetate to collect organic phases. The organic phases were combined, dried over anhydrous sodium sulfate, and filtered to collect a filtrate. The filtrate was subjected to vacuum distillation, and a solvent was recovered, obtaining a crude product.

The crude product was dissolved in 1,4-dioxane (200 mL), and a 10 wt % aqueous solution of sodium carbonate (7.95 g, 75 mmol) was added, and then Fmoc-Osu (18.50 g, 55 mol) was added dropwise. A resulting material was subjected to a reaction by stirring at ambient temperature for 2 h. After the reaction was completed, hydrochloric acid (2 mol/L) was added to a resulting product system until a pH value of the system was 7. A resulting material was subjected to extraction 3 times with 500 mL of ethyl acetate to collect organic phases. The organic phases were combined, washed with saturated sodium chloride solution, dried over anhydrous sodium sulfate, and filtered to obtain a filtrate. The filtrate was subjected to vacuum distillation, and a solvent was recovered, obtaining a crude product. The crude product was subjected to separation and purification by silica gel column chromatography (using 200-300 mesh silica gel and a mixed solvent of ethyl acetate and petroleum ether with a volume ratio of 40:60 as an eluent) to obtain 16.45 g of a colorless oily liquid, namely the compound 4, with a yield of 80%.

Compound 4 was Synthesized Using Compound 2':

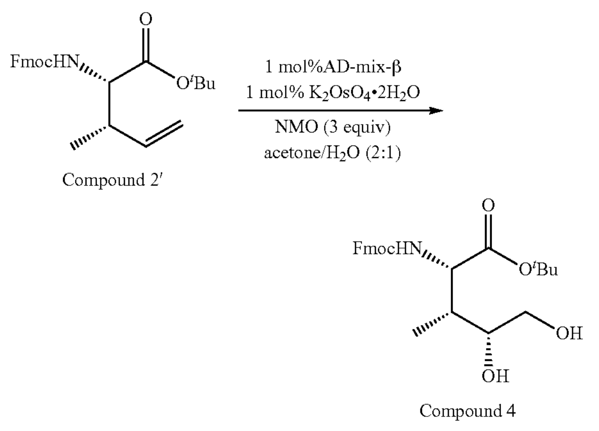

Compound 2'
Compound 4

$K_2OsO_4 \cdot 2H_2O$ (370 mg, 1 mol %), AD-mix-β (780 mg, 1 mol %), and 100 mL of acetone aqueous solution (a volume ratio of acetone to water was 2:1) were mixed, and a resulting material was stirred for 10 min, and then NMO (35.1 g, 0.3 mol), the compound 2 (40.7 g, 0.1 mol), and 300 mL of acetone aqueous solution (a volume ratio of acetone to water was 2:1) were added thereto. A resulting material was subjected to a reaction by stirring at ambient temperature for 12 h. After the reaction was completed, an excess of saturated $Na_2SO_3$ solution was added to quench the reaction. A resulting material was extraction 3 times with 500 mL of ethyl acetate to collect organic phases. The organic phases were combined, washed with saturated sodium chloride solution, dried over anhydrous sodium sulfate, and filtered to collect a filtrate. The filtrate was subjected to vacuum distillation, and a solvent was recovered, obtaining a crude product. The crude product was subjected to separation and purification by silica gel column chromatography (using 200-300 mesh silica gel and a mixed solvent of ethyl acetate and petroleum ether in a volume ratio of 35:65 as an eluent) to obtain 3.06 g of a light yellow oily liquid, namely the compound 4, with a yield of 82%.

The chemical name of the compound 4 was (2S,3R,4R)-2-((((9H-fluoren-9-yl)methoxy)carbonyl)amino)-4,5-dihydroxy-3-tert-butyl methylvalerate. The compound 4 was subjected to HPLC analysis, and the results were shown in Tables 3 and 4. The conditions of the HPLC analysis included: DAICEL CHIRALPAK IC; a mobile phase was n-hexane and isopropanol, and a volume ratio of the n-hexane to isopropanol was 95:5; a detection wavelength was 254 nm, and a flow rate of the mobile phase was 1.0 mL/min; $tR_1$=13.248 min (major), $tR_2$=34.663 min (minor). The results showed that the dr value was 10:1 and the ee value was 99%

TABLE 3

HPLC analysis data corresponding to racemic product of compound 4

| Peak | Retention time (min) | Height (mAU) | Area (%) |
|---|---|---|---|
| 1 | 14.497 | 18.399 | 40.22 |
| 2 | 15.307 | 1.052 | 2.43 |
| 3 | 19.500 | 2.732 | 7.24 |
| 4 | 21.285 | 1.228 | 4.21 |
| 5 | 24.347 | 2.054 | 7.18 |
| 6 | 36.120 | 6.905 | 38.71 |

TABLE 4

HPLC analysis data corresponding to chiral product of compound 4

| Peak | Retention time (min) | Height (mAU) | Area (%) |
|---|---|---|---|
| 1 | 13.572 | 146.448 | 97.79 |
| 2 | 18.610 | 1.131 | 0.94 |
| 3 | 20.387 | 1.382 | 1.21 |
| 4 | 35.443 | 0.214 | 0.06 |

The NMR data of the compound 4 were as follows:

$^1$H NMR (600 MHz, $CDCl_3$) δ 7.75 (dd, J=7.5, 3.8 Hz, 2H), 7.58 (d, J=7.5 Hz, 2H), 7.42-7.36 (m, 2H), 7.31 (t, J=7.4 Hz, 1H), 5.77 (d, J=7.9 Hz, 1H), 4.93 (s, 1H), 4.68 (d, J=2.2 Hz, 1H), 4.48 (dd, J=10.7, 7.1 Hz, 1H), 4.38 (dd, J=10.7, 6.8 Hz, 1H), 4.20 (t, J=6.9 Hz, 1H), 3.75 (dd, J=11.2, 2.3 Hz, 1H), 3.52 (dd, J=11.2, 7.0 Hz, 1H), 3.25 (t, J=7.4 Hz, 1H), 2.72 (s, 1H), 2.20-2.11 (m, 1H), 1.47 (s, 9H), 0.72 (d, J=6.9 Hz, 3H). $^{13}$C NMR (151 MHz, $CDCl_3$) δ 171.1, 157.8, 143.7, 143.5, 141.4, 141.4, 127.8, 127.2, 127.2, 125.1, 124.9, 120.1, 120.0, 82.8, 72.5, 67.5, 64.3, 55.1, 47.2, 39.4, 28.0, 10.2. HRMS (ESI+) calcd. for $C_{25}H_{31}NNaO_6^+$ $(M+Na)^+$: 464.2044; found: 464.2032.

Example 4 Synthesis of Compound 5

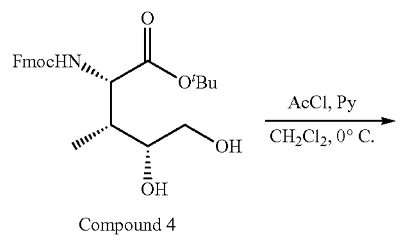

Compound 4

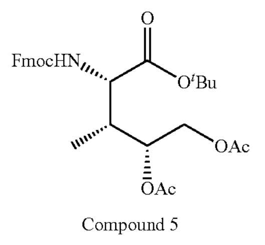

Compound 5

The compound 4 (22.0 g, 50 mmol) and pyridine (6.0 g, 75 mmol) were added into dry DCM (500 mL), stirred and dissolved at 0° C., and then acetyl chloride (8.6 g, 110 mmol) was added dropwise at 100 mL/h. A resulting material was stirred and reacted at 0° C. for 1 h, and then heated to ambient temperature and stirred and reacted for 1 h. After the reaction, a resulting product system was washed with a saturated $NH_4Cl$ solution, and an organic phase was collected. The organic phase was dried over anhydrous sodium sulfate, and filtered to collect a filtrate. The filtrate was subjected to vacuum distillation, and a solvent was recovered, obtaining a crude product. The crude product was subjected to separation and purification by silica gel column chromatography (using 200-300 mesh silica gel and a mixed solvent of ethyl acetate and petroleum ether with a volume ratio of 8:92 as an eluent) to obtain 22.0 g of a white solid, namely the compound 5, with a yield of 84%.

The chemical name of the compound 5 was (2R,3R,4R)-4-((((9H-fluoren-9-yl)methoxy)carbonyl)amino)-5-(tert-butoxy)-3-methyl-5-oxopentan-1,2-diacetyl diacetate, and NMR data thereof were as follows:

$^1$H NMR (600 MHz, $CDCl_3$) δ 7.76 (d, J=7.5 Hz, 2H), 7.61 (dd, J=11.6, 7.6 Hz, 2H), 7.39 (t, J=7.4 Hz, 2H), 7.31 (t, J=7.4 Hz, 2H), 5.24 (d, J=9.9 Hz, 1H), 4.84 (d, J=9.2 Hz, 1H), 4.65 (dd, J=9.8, 2.2 Hz, 1H), 4.48 (d, J=11.4 Hz, 1H), 4.35 (dt, J=17.9, 10.5 Hz, 2H), 4.22 (t, J=7.1 Hz, 1H), 4.09 (dd, J=12.4, 4.5 Hz, 1H), 2.54-2.45 (m, 1H), 2.11 (s, 3H), 2.08 (s, 3H), 1.50 (s, 9H), 0.91 (d, J=7.1 Hz, 3H). $^{13}$C NMR (151 MHz, $CDCl_3$) δ 170.9, 170.8, 170.5, 156.4, 144.1, 143.9, 141.4, 141.4, 127.8, 127.8, 127.2, 125.4, 125.2, 120.1, 120.0, 82.7, 71.9, 67.4, 63.4, 54.8, 47.3, 36.2, 28.2, 21.2, 20.9, 11.1. HRMS (ESI+) calcd. for $C_{29}H_{35}NNaO_8^+$ $(M+Na)^+$: 548.2255; found: 548.2262.

Example 5 Synthesis of Compound 6

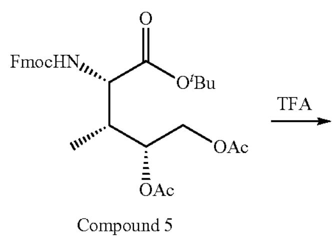

Compound 5

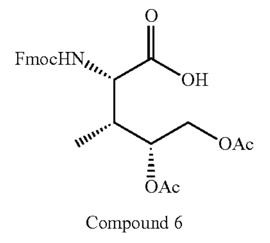

Compound 6

A compound 5 (21.01 g, 40 mmol) was mixed with TFA (50 mL). A resulting mixture was subjected to a reaction by stirring at ambient temperature for 2 h, and the compound 5 was completely reacted by TLC monitoring. After the reaction was completed, a resulting product system was subjected to vacuum distillation, and a solvent was recovered, obtaining a crude product. The crude product was subjected to separation and purification by silica gel column chromatography (using 200-300 mesh silica gel and a mixed solvent of methanol and DCM with a volume ratio of 5:95 as an eluent) to obtain 16.89 g of a white solid, namely the compound 6, with a yield of 90%.

The chemical name of the compound 6 was (2S,3R,4R)-2-((((9H-fluoren-9-yl)methoxy)carbonyl)amino)-4,5-diacetoxy-3-methylvaleric acid, and NMR data thereof were as follows:

$^1$H NMR (600 MHz, DMSO) δ 13.05 (s, 1H), 7.88 (d, J=7.2 Hz, 2H), 7.74 (dd, J=18.8, 7.2 Hz, 2H), 7.65 (d, J=9.4 Hz, 1H), 7.41 (t, J=7.0 Hz, 2H), 7.33 (d, J=4.6 Hz, 2H), 4.77 (d, J=7.5 Hz, 1H), 4.48-4.44 (m, 1H), 4.38 (d, J=11.9 Hz, 1H), 4.28-4.24 (m, 1H), 4.22-4.15 (m, 2H), 4.05 (dd, J=12.1, 4.3 Hz, 1H), 3.43 (s, 1H), 2.00 (s, 3H), 1.96 (s, 3H), 0.93 (d, J=6.6 Hz, 3H). $^{13}$C NMR (151 MHz, DMSO) δ 173.1, 170.2, 169.7, 156.6, 144.1, 143.7, 140.7, 140.7, 127.7, 127.6, 127.2, 127.1, 125.6, 125.3, 120.1, 120.1, 71.5, 66.0, 62.8, 54.1, 46.7, 39.5, 34.9, 20.7, 20.6, 10.9. HRMS (ESI+) calcd. for $C_{25}H_{27}NNaO_8^+$ $(M+Na)^+$: 492.1629; found: 492.1635.

It can be seen from the above examples that the efficient asymmetric synthesis of a (2S,3R,4R)-4,5-DHile derivative is achieved by using benzophenone imine glycine tert-butyl ester as a starting reaction raw material through asymmetric allylation, asymmetric dihydroxylation, and introduction or removal of protective groups. At the same time, the synthesis of enantiomers and diastereomers of the (2S,3R,4R)-4,5-DHile derivative can be achieved for the first time. The asymmetric allylation of the benzophenone imine glycine tert-butyl ester with 3-chlorobut-1-ene is catalyzed by $[Rh(COD)Cl]_2$ catalyst, $Cu(CH_3CN)_4PF_6$ catalyst, josiphos ligand, and tBu-PHOX ligand to generate an allyl-substituted glycine derivative. Then, N-Fmoc-(2S,3R,4R)-4,5-DHile is synthesized through asymmetric dihydroxylation, imine hydrolysis, Fmoc protection, and tert-butyl ester hydrolysis. The raw materials and reagents used are easily available, and the method has mild reaction conditions, simple operations, high stereoselectivity, and an enantiomeric excess (ee) of up to 99%. Moreover, the separation and purification process shows desirable operability and high total yield, and is of significant application value in the field of amino acid derivative synthesis.

The above descriptions are merely preferred implementations of the present disclosure. It should be noted that a person of ordinary skill in the art may further make several improvements and modifications without departing from the principle of the present disclosure, but such improvements and modifications should be deemed as falling within the scope of the present disclosure.

What is claimed is:

1. A method for preparing an intermediate A of a (2S,3R,4R)-4,5-dihydroxyisoleucine (DHile) derivative, comprising the following steps:

subjecting a compound 1 with 3-chlorobut-1-ene to asymmetric allylation to obtain the intermediate A of the (2S,3R,4R)-4,5-DHile derivative;

wherein the compound 1 has a structure shown in Formula 1, and the intermediate A of the (2S,3R,4R)-4,5-DHile derivative has a structure shown in Formula 2:

Formula 1

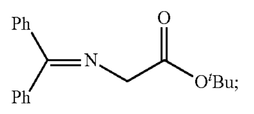

-continued

Formula 2

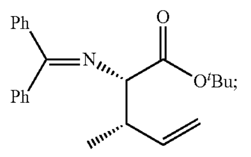

the asymmetric allylation is conducted in the presence of a rhodium catalyst, a rhodium catalyst ligand, a copper catalyst, a copper catalyst ligand, and an alkaline reagent;

the rhodium catalyst is $[Rh(COD)C1]_{2,}$ the copper catalyst is Cu $(CH_3CN)_4PF_{6,}$ and the alkaline reagent is potassium phosphate;

the rhodium catalyst ligand has a structure shown below:

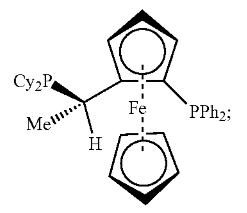

and the copper catalyst ligand has a structure shown below:

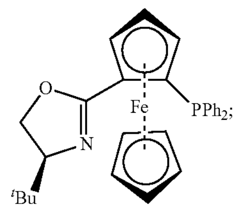

and the asymmetric allylation is conducted at a temperature of −10° C. to 25° C. for 12 hours to 24 hours.

2. A method for preparing a (2S,3R,4R)-4,5-DHile derivative, comprising the following steps:

preparing the intermediate A of the (2S,3R,4R)-4,5-DHile derivative by the method of claim 1;

subjecting the intermediate A of the (2S,3R,4R)-4,5-DHile derivative to asymmetric dihydroxylation to obtain an intermediate B of the (2S,3R,4R)-4,5-DHile derivative;

subjecting the intermediate B of the (2S,3R,4R)-4,5-DHile derivative to imine hydrolysis and 9-fluorenylmethoxycarbonyl (Fmoc) protection to obtain an intermediate C of the (2S,3R,4R)-4,5-DHile derivative;

subjecting the intermediate C of the (2S,3R,4R)-4,5-DHile derivative to acetylation to obtain an intermediate D of the (2S,3R,4R)-4,5-DHile derivative; and subjecting the intermediate D of the (2S,3R,4R)-4,5-DHile derivative to tert-butyl ester hydrolysis to obtain the (2S,3R,4R)-4,5-DHile derivative;

wherein the intermediate B of the (2S,3R,4R)-4,5-DHile derivative, the intermediate C of the (2S,3R,4R)-4,5-DHile derivative, the intermediate D of the (2S,3R,4R)-4,5-DHile derivative, and the (2S,3R,4R)-4,5-DHile derivative have structures shown in Formula 3, Formula 4, Formula 5, and Formula 6, respectively:

Formula 3

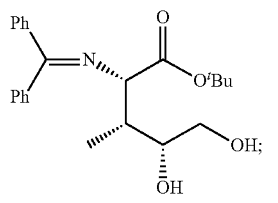

Formula 4

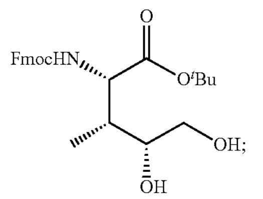

Formula 5

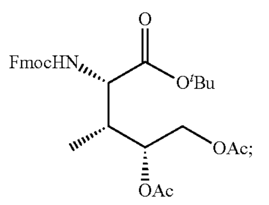

Formula 6

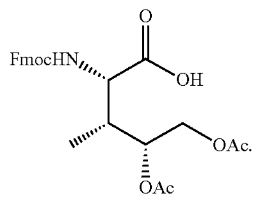

3. A method for preparing a (2S,3R,4R)-4,5-DHile derivative, comprising the following steps:

preparing the intermediate A of the (2S,3R,4R)-4,5-DHile derivative by the method of claim 1;

subjecting the intermediate A of the (2S,3R,4R)-4,5-DHile derivative to imine hydrolysis and Fmoc protection to obtain an intermediate A' of the (2S,3R,4R)-4,5-DHile derivative;

subjecting the intermediate A' of the (2S,3R,4R)-4,5-DHile derivative to asymmetric dihydroxylation to obtain an intermediate C of the (2S,3R,4R)-4,5-DHile derivative;

subjecting the intermediate C of the (2S,3R,4R)-4,5-DHile derivative to acetylation to obtain an intermediate D of the (2S,3R,4R)-4,5-DHile derivative; and subjecting the intermediate D of the (2S,3R,4R)-4,5-DHile derivative to tert-butyl ester hydrolysis to obtain the (2S,3R,4R)-4,5-DHile derivative;

wherein the intermediate A' of the (2S,3R,4R)-4,5-DHile derivative, the intermediate C of the (2S,3R,4R)-4,5-DHile derivative, the intermediate D of the (2S,3R,4R)-4,5-DHile derivative, and the (2S,3R,4R)-4,5-DHile derivative have structures shown in Formula 2', Formula 4, Formula 5, and Formula 6, respectively:

Formula 2′

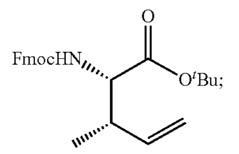

Formula 4

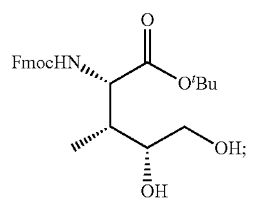

Formula 5

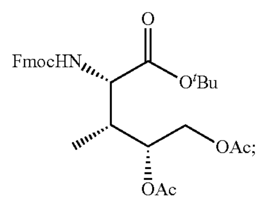

Formula 6

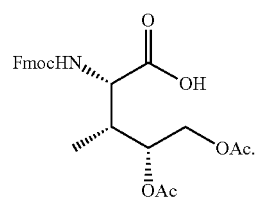

4. An intermediate for synthesizing a (2S,3R,4R)-4,5-DHile derivative, wherein the intermediate is a compound having a structure shown in Formula 3:

Formula 3

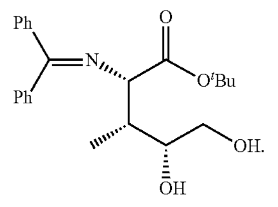

* * * * *